(12) United States Patent
Choi et al.

(10) Patent No.: US 9,327,276 B2
(45) Date of Patent: May 3, 2016

(54) CATALYST FOR GLYCERIN DEHYDRATION, PREPARATION METHOD THEREOF, AND PREPARATION METHOD OF ACROLEIN

(71) Applicant: LG CHEM, LTD., Seoul (KR)

(72) Inventors: Jun Seon Choi, Daejeon (KR); Ji Yeon Kim, Daejeon (KR); Joo Young Cheon, Daejeon (KR); Wang Rae Joe, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/440,270

(22) PCT Filed: Jul. 15, 2014

(86) PCT No.: PCT/KR2014/006395
§ 371 (c)(1),
(2) Date: May 1, 2015

(87) PCT Pub. No.: WO2015/009032
PCT Pub. Date: Jan. 22, 2015

(65) Prior Publication Data
US 2015/0298105 A1    Oct. 22, 2015

(30) Foreign Application Priority Data

Jul. 16, 2013 (KR) .................. 10-2013-0083542
Jul. 14, 2014 (KR) .................. 10-2014-0088480

(51) Int. Cl.
| | | |
|---|---|---|
| *C07C 45/29* | (2006.01) | |
| *B01J 37/00* | (2006.01) | |
| *B01J 27/00* | (2006.01) | |
| *B01J 27/195* | (2006.01) | |
| *C07C 29/60* | (2006.01) | |
| *C07C 45/52* | (2006.01) | |
| *B01J 37/02* | (2006.01) | |
| *B01J 37/08* | (2006.01) | |
| *B01J 27/053* | (2006.01) | |
| *B01J 27/055* | (2006.01) | |
| *B01J 27/188* | (2006.01) | |
| *B01J 37/04* | (2006.01) | |
| *B01J 37/20* | (2006.01) | |
| *B01J 37/28* | (2006.01) | |

(52) U.S. Cl.
CPC .............. *B01J 27/195* (2013.01); *B01J 27/053* (2013.01); *B01J 27/055* (2013.01); *B01J 27/188* (2013.01); *B01J 37/0236* (2013.01); *B01J 37/04* (2013.01); *B01J 37/08* (2013.01); *C07C 29/60* (2013.01); *C07C 45/29* (2013.01); *C07C 45/52* (2013.01); *B01J 37/20* (2013.01); *B01J 37/28* (2013.01); *B01J 2523/00* (2013.01)

(58) Field of Classification Search
CPC .......... C07C 45/29; C07C 45/52; B01J 37/04; B01J 27/186
USPC .................................. 568/486; 502/210, 219
See application file for complete search history.

(56) References Cited

FOREIGN PATENT DOCUMENTS

| | | |
|---|---|---|
| JP | 2010-99596 | 5/2010 |
| KR | 10-2011-0011603 | 10/2010 |
| KR | 10-2011-0004872 | 1/2011 |
| KR | 10-2011-0077007 | 5/2011 |
| KR | 10-2011-0094198 | 6/2011 |
| KR | 10-2012-0093853 | 4/2012 |
| KR | 10-2013-0071224 | 6/2013 |
| WO | 2012101526 A1 | 8/2012 |

OTHER PUBLICATIONS

Chai, Song-Hai et al., Sustainable production of acrolein: Preparation and characterization of zirconia-supported 12-tungstophosphoric acid catalyst for gas-phase dehydration of glycerol, Applied Catalysis A: General, Feb. 1, 2009, vol. 353, No. 2, p. 213-222.

*Primary Examiner* — Sikarl Witherspoon
(74) *Attorney, Agent, or Firm* — Dentons US LLP

(57) ABSTRACT

The present invention relates to a catalyst for glycerin dehydration, a preparation method thereof, and a preparation method of acrolein, and more particularly, to a catalyst for glycerin dehydration which minimizes by-product formation during glycerin dehydration to improve acrolein selectivity and maintains high catalytic activity during reaction.

17 Claims, No Drawings

CATALYST FOR GLYCERIN DEHYDRATION, PREPARATION METHOD THEREOF, AND PREPARATION METHOD OF ACROLEIN

This application is a National Stage Entry of International Application No. PCT/KR2014/006395, filed Jul. 15, 2014, which claims priority to and the benefit of Korean Application No. 10-2013-0083542, filed on Jul. 16, 2013 and Korean Patent Application No. 10-2014-0088480 filed Jul. 14, 2014, all of which are hereby incorporated by reference in their entirety.

TECHNICAL FIELD

The present invention relates to a catalyst for glycerin dehydration, a preparation method thereof, and a preparation method of acrolein, and more particularly, to a catalyst for glycerin dehydration which minimizes by-product formation to improve acrolein selectivity and maintains high catalytic activity during reaction, a preparation method thereof, and a preparation method of acrolein.

BACKGROUND OF ART

Acrolein is a simple unsaturated aldehyde compound which includes incomplete reactive groups to have high reactivity, and is used as a major intermediate for synthesis of numerous chemicals. In particular, acrolein has been widely used as an intermediate for synthesis of acrylic acids, acrylic acid esters, superabsorbent polymers, animal feed supplements, or food supplements.

Such acrolein has been mainly prepared by selective gas-phase oxidation of a starting material, propylene, which is obtained during petroleum cracking with atmospheric oxygen. However, as fossil fuels have been reduced and environmental problems such as the greenhouse effect have emerged, many studies have been conducted to develop a method of preparing acrolein using non-fossil fuel-based renewable materials.

Therefore, glycerin, which is a natural by-product obtained from biodiesel production, has received much attention as a raw material for acrolein preparation. In particular, the growth of biodiesel production increases the glycerin market, and industrial application of glycerin has been studied due to its low price.

For example, a method of obtaining a mixture of acrolein and acrylic acid by glycerin dehydration in the presence of a catalyst is known. The glycerin dehydration is performed by gas-phase oxidation in the presence of a catalyst, and use of the catalyst is essential. However, the previous catalysts used for the preparation of acrolein produce by-products such as hydroxypropanone, propane aldehyde, acetaldehyde, acetone, and polycondensation products of glycerin, or cyclic glycerin ether, and thus there are limitations in their use for the preparation of acrolein with high purity. In addition, the previous catalysts produce phenol or a polyaromatic compound as a by-product, which problematically causes coke formation on the catalyst and catalyst deactivation.

Accordingly, there is a demand to develop a catalyst system capable of maintaining high catalytic activity during reaction while minimizing formation of by-products causing such problems so as to increase selectivity and purity of acrolein and improve glycerin conversion ratio and reaction yield.

DETAILED DESCRIPTION OF THE INVENTION

Technical Problem

An object of the present invention is to provide a catalyst for glycerin dehydration, which is able to minimize by-product formation to increase acrolein selectivity and to maintain high catalytic activity during reaction.

Another object of the present invention is to provide a preparation method of the catalyst for glycerin dehydration.

Still another object of the present invention is to provide a preparation method of acrolein using the catalyst for glycerin dehydration.

Technical Solution

The present invention provides a catalyst for glycerin dehydration including a composite metal oxide represented by the following Chemical Formula 1:

$(Ma)_p(Mb)_q WA_r O_x$          [Chemical Formula 1]

wherein A is phosphorus or sulfur,

Ma and Mb may be the same as or different from each other and are each independently Zr, Ti, Ce, Nb, Cr, Mo, Mn, Zn, B, or Cu, and p and q are each independently a real number of 0 to 3, when either one of Ma and Mb is B, the other is Zr, Ti, Ce, Nb, Cr, Mo, Mn, Zn, or Cu, and p and q are a real number of more than 0 and 3 or less, r is a real number of 1 to 3, and x is a real number of 1 to 20.

Further, the present invention provides a preparation method of the catalyst for glycerin dehydration, including the steps of mixing one or more selected from the group consisting of a phosphorus precursor and a sulfur precursor with a tungsten precursor; and drying and calcinating the mixture.

Furthermore, the present invention provides a preparation method of acrolein, including the step of reacting glycerin in the presence of the catalyst for glycerin dehydration.

Hereinafter, a catalyst for glycerin dehydration, a preparation method thereof, and a preparation method of acrolein according to specific embodiments of the present invention will be described in more detail.

As used herein, the term "glycerin dehydration" means an overall process by which water is separated from a glycerin molecule or between glycerin molecules.

According to an embodiment of the present invention, a catalyst for glycerin dehydration including a composite metal oxide represented by Chemical Formula 1 is provided.

The present inventors recognized that in the known method of preparing acrolein by gas-phase oxidation of a starting material, propylene has limitations of reduced fossil fuel stocks and environmental problems such as the greenhouse effect, and therefore they have studied on a method of preparing acrolein using environmentally friendly and renewable raw materials. As a result, they found that glycerin dehydration can be performed in the presence of a catalyst including a composite metal oxide containing phosphorus or sulfur and tungsten so as to prepare acrolein with a high yield and a high conversion ratio while minimizing by-product formation, thereby completing the present invention.

In particular, although the composite metal oxide is a simple oxide containing phosphorus or sulfur and tungsten at a predetermined ratio, it is able to remarkably reduce by-product formation to increase the yield of acrolein, compared to the vanadium-containing catalysts for glycerin dehydration or acrolein preparation previously used. In particular, when the composite metal oxide is used, production of hydroxypropanone which is a major by-product of glycerin dehydration, may be greatly reduced.

Furthermore, the previous catalysts produce phenol or a polyaromatic compound as a by-product, which problematically causes the coke formation on the catalyst and catalyst deactivation. However, the catalyst for glycerin dehydration inhibits formation of the above-described by-products, thereby maintaining high catalytic activity during reaction.

The catalyst for glycerin dehydration having such characteristics may include a composite metal oxide represented by the following Chemical Formula 1:

$$(Ma)_p(Mb)_pWA_rO_x \quad \text{[Chemical Formula 1]}$$

wherein A is phosphorus (P) or sulfur (S),

Ma and Mb may be the same as or different from each other and are each independently Zr, Ti, Ce, Nb, Cr, Mo, Mn, Zn, B, or Cu, and p and q are each independently a real number of 0 to 3, when either one of Ma and Mb is B, the other is Zr, Ti, Ce, Nb, Cr, Mo, Mn, Zn, or Cu, and p and q are a real number of more than 0 and 3 or less.

Further, r is a real number of 1 to 3, and x is a real number of 1 to 20.

Meanwhile, a molar ratio of phosphorus or sulfur represented by A and tungsten in the composite metal oxide may be 10:1 to 1:10, and preferably 5:1 to 1:1. Since the composite metal oxide includes phosphorus or sulfur and tungsten as essential elements, in particular, at the above molar ratio, these elements strongly bind to each other to function as acid sites that donate protons or accept unshared electron pairs. Therefore, the composite metal oxide may dehydrate glycerin with higher selectivity, conversion ratio, and yield so as to prepare acrolein.

In the composite metal oxide, the phosphorus or sulfur and tungsten bind with oxygen, respectively, and exist in oxide forms such as phosphate ($PO_4$), sulfate ($SO_4$), or tungstate ($WO_4$). In particular, the elements of the composite metal oxide bind as the oxide form to increase acid sites such as Brönsted or Lewis acid sites, leading to more effective glycerin dehydration.

In the composite oxide, the content of oxygen and the X value of Chemical Formula 1 may be properly controlled depending on contents of phosphorus or sulfur and tungsten and components further added, and a composition ratio thereof. Specifically, a molar ratio of phosphorus or sulfur and tungsten to oxygen may be 1:1 to 1:5. In this regard, the molar ratio of phosphorus or sulfur and tungsten to oxygen corresponds to a ratio of the total number of moles of phosphorus or sulfur and tungsten to the number of moles of oxygen.

The composite metal oxide represented by Chemical Formula 1 may further include a second metal represented by Ma or Mb, in addition to phosphorus or sulfur and tungsten, copper, and tungsten. Specifically, the second metal may be one or more metals selected from the group consisting of Zr, Ti, Ce, Nb, Cr, Mo, Mn, Zn, B, and Cu. The term "second" is used to distinguish the above metals from phosphorus, sulfur, and tungsten, and does not mean the reaction order or priority.

In the composite metal oxide, the second metal binds to oxygen with phosphorus or sulfur, and tungsten. The composite metal oxide further includes the second metal, thereby remarkably improving acrolein selectivity and inhibiting formation of a hydroxypropanone by-product. In particular, if boron or niobium is included as the second metal, the second metal inhibits by-product formation and also functions as an acid site capable of causing glycerin dehydration, leading to more effective glycerin dehydration for acrolein preparation.

A molar ratio of the second metal represented by Ma or Mb to tungsten may be 10:1 to 1:10. If the content of the second metal is too small, improvement of the acrolein selectivity may be very slight. Even if the content of the second metal is too large, the increased metal content may not bring out significant improvement in the catalytic activity or selectivity, which is economically unfavorable.

Meanwhile, in the composite metal oxide of an embodiment, when any one of Ma and Mb in Chemical Formula 1 is B, the other is Zr, Ti, Ce, Nb, Cr, Mo, Mn, Zn, or Cu, and p and q may be a real number of more than 0 and 3 or less. That is, Ma and Mb are different from each other. When either one of Ma and Mb is boron (B), the other of Ma and Mb may be Zr, Ti, Ce, Nb, Cr, Mo, Mn, Zn, or Cu, but not boron (B). In this regard, p and q indicating the contents of Ma and Mb are more than 0 and 3 or less.

Further, in the composite metal oxide represented by Chemical Formula 1, if Ma and Mb are the same as each other, Ma and Mb may be Zr, Ti, Ce, Nb, Cr, Mo, Mn, Zn, or Cu. In this case, the two elements may be the same as each other, but Ma or Mb in Chemical Formula 1 may exist singly if p or q is 0.

Further, specific examples of the composite metal oxide may include $CuWS_3O_x$, $CuBWS_3O_x$, $CuB_{0.4}WS_3O_x$, $NbBWP_2O_x$, $Nb_{0.5}BWP_2O_x$, $Nb_{0.7}BWP_2O_x$, $NbB_{0.5}WP_2O_x$, $NbB_{0.7}WP_2O_x$, $Ce_{0.25}B_{0.25}WO_2O_x$, $Ce_{0.25}B_{0.5}WP_2O_x$, $Ce_{0.25}B_{0.75}WP_2O_x$, $Ce_{0.25}BWP_2O_x$, $Ce_{0.5}BWP_2O_x$, $NbCeBWP_3O_x$, $Cu_{0.2}B_{0.867}W_{0.5}PO_x$, or mixtures thereof.

The catalyst for glycerin dehydration may further include a support onto which the composite metal oxide is immobilized. Any support that is known to be used in a typical catalyst may be used without limitations. Specific examples of the support may include silica, alumina, silica-alumina, zirconia, magnesia, magnesium aluminate, calcium aluminate, silicon carbide, zirconium phosphate, zeolite, or mixtures thereof. Preferably, silica having a pore size of 20 nm or more may be used.

The support may function to immobilize the composite metal oxide containing one or more atoms selected from the group consisting of phosphorus and sulfur, and tungsten, and the composite metal oxide may be immobilized on the support with a large surface area by sharing oxygen therewith. When the composite metal oxide is prepared by immobilizing it on the support, it is easier to store and transport, and a large amount of glycerin may be effectively reacted due to the large surface area.

The support may have a specific surface area of 10 to 500 $m^2/g$, and preferably 50 to 200 $m^2/g$. In particular, the catalyst for glycerin dehydration prepared by supporting the composite metal oxide on the support having a large specific surface area within the above range has a proper pore size, thereby reducing coke deposition and providing sufficient catalytic activity.

The catalyst for glycerin dehydration may include 1 to 50 parts by weight of the composite metal oxide containing one or more atoms selected from the group consisting of phosphorus and sulfur, and tungsten, based on 100 parts by weight of the support.

According to another embodiment of the present invention, a preparation method of the catalyst for glycerin dehydration including the steps of mixing one or more selected from the group consisting of a phosphorus precursor and a sulfur precursor with a tungsten precursor, and drying and calcinating the mixture, is provided.

This preparation method may be used to provide the above-described catalyst for glycerin dehydration of an embodiment of the present invention. As described above, this catalyst is able to minimize by-product formation during glycerin dehydration, thereby preparing acrolein with high selectivity, and is able to inhibit production of phenol or a polyaromatic compound which causes catalyst deactivation, thereby maintaining high catalytic activity.

The phosphorus precursor, sulfur precursor, and tungsten precursor collectively refer to substances for providing phosphorus, sulfur, and tungsten that are included in the catalyst for glycerin dehydration, respectively. For example, they may be in the form of an oxide or salt containing any one of phosphorus, sulfur, and tungsten.

More specifically, the tungsten precursor may be a hydrochloride or hydrochloride oxide containing tungsten, tungstic acid containing tungstate anions, tungstate acid, metatungstate, or paratungstate. The phosphorus precursor may be phosphoric acid containing phosphate anions ($PO_4^-$), or a phosphate such as ammonium phosphate, hydrogen phosphate, or dihydrogen phosphate. The sulfur precursor may be sulfuric acid containing sulfate anions ($SO_4^-$), or a sulfate such as ammonium sulfate or hydrogen sulfate.

A mixing molar ratio of one or more selected from the group consisting of the phosphorus precursor and the sulfur precursor, and the tungsten precursor, may be 10:1 to 1:10. As described above, in the catalyst for glycerin dehydration, phosphorus or sulfur and tungsten strongly bind to each other to function as acid sites that donate protons or accept unshared electron pairs, and therefore, glycerin may be dehydrated with higher selectivity and yield so as to prepare acrolein.

In the step of mixing one or more selected from the group consisting of the phosphorus precursor and the sulfur precursor with the tungsten precursor, one or more second metal precursors selected from the group consisting of Zr, Ti, Ce, Nb, Cr, Mo, Mn, Zn, B, and Cu may be further included and mixed with the phosphorus precursor, sulfur precursor, and tungsten precursor. The above descriptions may also be applied to a specific example of the second metal and a mixing ratio thereof without limitation.

Next, the preparation method of the catalyst for glycerin dehydration may include the step of drying and calcinating a mixture which is prepared by mixing one or more selected from the group consisting of the phosphorus precursor and the sulfur precursor with the tungsten precursor.

In more detail, in the drying step, the mixture is dried at 100° C. or higher for 10 minutes to 24 hours to remove the solvent from the mixture, before calcination. In this drying process, a drying method and a drying device which are known to be typically used may be used, and for example, a heat source such as a hot air dryer, an oven, a heating plate, etc. may be used to perform the drying process.

Further, the calcinating step means a process of preparing a curable material by heating a reactant at a high temperature, and may be performed at a temperature ranging from 100 to 900° C., preferably from 250 to 750° C. At a temperature lower than the above range, the structure and degree of crystallization of the catalyst may be changed during reaction. At a temperature higher than the above range, interactions between atoms become too strong, and thus their particle size may increase or unnecessary side reactions may occur.

The drying and calcinating steps may be performed for 10 minutes to 10 hours, respectively. If the drying and calcinating times are too short, the catalyst may not be completely dried and calcined, and if the drying and calcinating times are too long, various side reactions such as carbonization of the catalyst may occur.

The preparation method of the catalyst for glycerin dehydration of an embodiment may further include a step of supporting the mixture of one or more selected from the group consisting of the phosphorus precursor and the sulfur precursor with the tungsten precursor on a support. The step of supporting the mixture on the support may be performed by any method known in the art without limitation, and for example, an impregnation method or a powder mixing method may be used. Further, the above descriptions may also be applied to a specific example of the support and a mixing ratio thereof without limitation.

The impregnation method is a process of preparing the support in the form of spheres or pellets, and then aging and calcinating the support with the mixture containing the gel-type precipitate. The powder mixing method is a process of calcinating and supporting a mixture which is obtained by mixing the powdery support with the powdery resultant resulting from the aging and drying processes in the preparation process of the oxide catalyst.

That is, the catalyst for glycerin dehydration of an embodiment may be prepared by supporting the mixture on a support by the impregnation method or the powder mixing method. Thus, the mixture of one or more selected from the group consisting of the phosphorus precursor and the sulfur precursor, and the tungsten precursor, may be aged and calcined together with the spherical or pellet-type support for supporting, or the mixture may be aged and dried to prepare a powdery form, which may be mixed with the powdery support, followed by calcination for supporting.

Meanwhile, according to still another embodiment of the present invention, a preparation method of acrolein including the step of reacting glycerin in the presence of the above-described catalyst for glycerin dehydration is provided.

As described above, when the catalyst for glycerin dehydration of an embodiment of the present invention may be used, it is possible to perform glycerin dehydration with high acrolein selectivity, in particular, to minimize by-product formation, compared to use of the previously known catalysts.

The amount of the catalyst for glycerin dehydration may be properly controlled depending on the amount and concentration of glycerin, and for example, the catalyst may be used in an amount of 0.1 to 5 parts by weight, and preferably 1 to 3 parts by weight, based on 100 parts by weight of glycerin per hour.

Further, the dehydration reaction may be performed at a temperature of 200 to 400° C. Since the dehydration reaction is an endothermic reaction, the reaction may preferably be performed at a temperature within the above range in order to prepare acrolein with a high conversion ratio and selectivity.

Advantageous Effects

According to the present invention, a catalyst for glycerin dehydration which minimizes by-product formation to improve acrolein selectivity and maintains high catalytic activity during reaction, a preparation method thereof, and a preparation method of acrolein are provided.

DETAILED DESCRIPTION OF THE EMBODIMENTS

The present invention will be described in more detail with reference to the following examples. However, these examples are for illustrative purposes only, and the invention is not intended to be limited by these examples.

EXAMPLES

Preparation of Catalyst for Glycerin Dehydration

Example 1

6.16 g of a copper precursor (copper nitrate: $Cu(NO_3)_2 \cdot 3H_2O$), 6.22 g of a tungsten precursor (ammonium metatungstate: $(NH_4)_6W_{12}O_{36}$), and 10.1 g of a sulfur precursor (ammonium sulfate: $(NH_4)_2SO_4$) were dissolved in water to prepare a mixture, which was dried in an oven at 120° C., and then calcined at 500° C. for 3 hours to prepare a $CuWS_3O_x$ catalyst.

Examples 2 and 3

In Examples 2 and 3, 6.16 g of a copper precursor (copper nitrate: $Cu(NO_3)_2 \cdot 3H_2O$), 0.78 g of a boron precursor (boric acid: $H_3BO_3$), 6.22 g of a tungsten precursor (ammonium metatungstate: $(NH_4)_6W_{12}O_{36}$), and 10.1 g of a sulfur precursor (ammonium sulfate: $(NH_4)_2SO_4$) (Example 2); and 1.56 g of the copper precursor, 1.56 g of the boron precursor, 6.22 g of the tungsten precursor, and 10.1 g of a sulfur precursor (Example 3) were dissolved in water to prepare respective mixtures, which were dried in an oven at 120° C., and then calcined at 700° C. for 5 hours to prepare $CuB_{0.5}WS_3O_x$ and $CuBWS_3O_x$ catalysts, respectively.

Example 4

1.56 g of a boron precursor (boric acid: $H_3BO_3$), 6.22 g of a tungsten precursor (ammonium metatungstate: $(N_4)_6W_{12}O_{36}$), 8.02 g of a niobium precursor (ammonium niobium oxalate: $(NH_4)Nb(C_4O_4)$), and 5.88 g of a phosphorus precursor (phosphoric acid: $H_3PO_4$) were dissolved in water to prepare a mixture, which was dried in an oven at 120° C., and then calcined at 300° C. for 3 hours to prepare a $NbBWP_2O_x$ catalyst.

Example 5

A $NbBWP_2O_x$ catalyst was prepared in the same manner as in Example 7, except that calcination was performed at 700° C. for 5 hours.

Example 6

1.56 g of a boron precursor (boric acid: $H_3BO_3$), 6.22 g of a tungsten precursor (ammonium metatungstate: $(NH_4)_6W_{12}O_{36}$), 4.02 g of a niobium precursor (ammonium niobium oxalate: $(NH_4)Nb(C_4O_4)$), and 5.88 g of a phosphorus precursor (phosphoric acid: $H_3PO_4$) were dissolved in water to prepare a mixture, which was dried in an oven at 120° C., and then calcined at 500° C. for 3 hours to prepare a $Nb_{0.6}BWP_2O_x$ catalyst.

Example 7

1.56 g of a boron precursor (boric acid: $H_3BO_3$), 6.22 g of a tungsten precursor (ammonium metatungstate: $(NH_4)_6W_{12}O_{36}$), 5.62 g of a niobium precursor (ammonium niobium oxalate: $(NH_4)Nb(C_4O_4)$), and 5.88 g of a phosphorus precursor (phosphoric acid: $H_3PO_4$) were dissolved in water to prepare a mixture, which was dried in an oven at 120° C., and then calcined at 500° C. for 3 hours to prepare a $N_{0.7}BWP_2O_x$ catalyst.

Example 8

0.78 g of a boron precursor (boric acid: $H_3BO_3$), 6.22 g of a tungsten precursor (ammonium metatungstate: $(NH_4)_6W_{12}O_{36}$), 8.02 g of a niobium precursor (ammonium niobium oxalate: $(NH_4)Nb(C_4O_4)$), and 5.88 g of a phosphorus precursor (phosphoric acid: $H_3PO_4$) were dissolved in water to prepare a mixture, which was dried in an oven at 120° C., and then calcined at 500° C. for 3 hours to prepare a $NbB_{0.6}WP_2O_x$ catalyst.

Example 9

1.10 g of a boron precursor (boric acid: $H_3BO_3$), 6.22 g of a tungsten precursor (ammonium metatungstate: $(NH_4)_6W_{12}O_{36}$), 8.02 g of a niobium precursor (ammonium niobium oxalate: $(NH_4)Nb(C_4O_4)$), and 5.88 g of a phosphorus precursor (phosphoric acid: $H_3PO_4$) were dissolved in water to prepare a mixture, which was dried in an oven at 120° C., and then calcined at 500° C. for 3 hours to prepare a $NbB_{0.7}WP_2O_x$ catalyst.

Examples 10 to 14

In Examples 10 to 14, 2.77 g of a cerium precursor (cerium nitrate: $Ce(NO_3)_3 \cdot 6H_2O$), 0.39 g of a boron precursor (boric acid: $H_3BO_3$), 6.22 g of a tungsten precursor (ammonium metatungstate: $(NH_4)_6W_{12}O_{36}$), and 9.2 g of a phosphorus precursor (triethylphosphate: $(C_2H_5)_3 \cdot PO_4$) (Example 10); 2.77 g of the cerium precursor, 0.78 g of the boron precursor, 6.22 g of the tungsten precursor, and 9.2 g of the phosphorus precursor (Example 11); 2.77 g of the cerium precursor, 1.17 g of the boron precursor, 6.22 g of the tungsten precursor, and 9.2 g of the phosphorus precursor (Example 12); 2.77 g of the cerium precursor, 1.56 g of the boron precursor, 6.22 g of the tungsten precursor, and 9.2 g of the phosphorus precursor (Example 13); 5.54 g of the cerium precursor, 1.56 g of the boron precursor, 6.22 g of the tungsten precursor, and 9.2 g of the phosphorus precursor (Example 14) were dissolved in a mixture of water and ethanol, and dried in an oven at 120° C., and then calcined at 700° C. for 3 hours to prepare $Ce_{0.25}B_{0.25}WP_2O_x$, $Ce_{0.25}B_{0.5}WP_2O_x$, $Ce_{0.25}B_{0.75}WP_2O_x$, $Ce_{0.25}BWP_2O_x$, and $Ce_{0.5}BWP2O_x$ catalysts, respectively.

Example 15

11.08 g of a cerium precursor (cerium nitrate: $Ce(NO_3)_3 \cdot 6H_2O$), 1.56 g of a boron precursor (boric acid: $H_3BO_3$), 6.22 g of a tungsten precursor (ammonium metatungstate: $(NH_4)_6W_{12}O_{36}$), 8.02 g of a niobium precursor (ammonium niobium oxalate: $(NH_4)Nb(C_4O_4)$), and 8.82 g of a phosphorus precursor (phosphoric acid: $H_3PO_4$) were dissolved in a mixture of water and ethanol, and dried in an oven at 120° C., and then calcined at 700° C. for 3 hours to prepare a $NbCeBWP_3O_x$ catalyst.

Example 16

2.44 g of a copper precursor (copper nitrate: $Cu(NO_3)_2 \cdot 3H_2O$), 2.71 g of a boron precursor (boric acid: $H_3BO_3$), 6.22 g of a tungsten precursor (ammonium metatungstate: $(NH_4)_6W_{12}O_{36}$), and 9.2 g of a phosphorus precursor (triethylphosphate: $(C_2H_5)_3 \cdot PO_4$) were dissolved in a mixture of water and ethanol, and dried in an oven at 120° C., and then calcined at 700° C. for 3 hours to prepare a $Cu_{0.2}B_{0.867}W_{0.5}PO_x$ catalyst.

Comparative Examples 1 to 3

A zeolite-based commercial catalyst which is known to be used as a catalyst for dehydration was purchased from Zeolyst Co., and subjected to calcination at 600° C. for 3 hours before use.

Comparative Examples 4 to 5

A heteropolyacid-based commercial catalyst which is known to be used as a catalyst for dehydration was purchased from WAKO Co., and subjected to calcination at 300° C. for 3 hours before use.

Comparative Example 6

3.12 g of a boron precursor (boric acid: $H_3BO_3$) and 5.88 g of a phosphorus precursor (phosphoric acid: $H_3PO_4$) were dissolved in water to prepare a mixture at 60° C., which was dried under vacuum using a rotary evaporator to have a P/B ratio of 1. Then, calcination was performed at 700° C. for 6 hours to prepare a $BPO_4$ catalyst.

Experimental Example

Conversion Ratio of Glycerin, and Yield and Selectivity of Acrolein

An HTS (high-throughput screening) facility which was manufactured to evaluate performance using a small amount of the catalyst prepared in the examples or comparative examples in a short time under conditions given in the following Table 1 was used to prepare acrolein from glycerin, and the product was subjected to in-situ GC analysis to calculate conversion ratio, selectivity, and yield.

The conversion ratio of glycerin, and yield and selectivity of acrolein, are given in the following Tables 2 and 3.

Here, the conversion ratio represents a ratio of glycerin to converted compounds, the yield represents a conversion ratio of glycerin to acrolein, and the selectivity represents a ratio of acrolein to the converted compounds.

Further, comparative selectivity 1 represents a comparison of hydroxypropanone selectivity to acrolein selectivity, and comparative selectivity 2 represents a comparison of selectivity of hydroxypropanone, propionic acid, and aromatic compounds to acrolein selectivity. In comparative selectivity 1 or 2, hydroxypropanone is a major by-product in glycerin dehydration, and propionic acid and aromatic compounds are also by-products which may cause coke formation.

TABLE 1

Conditions for glycerin dehydration

| | |
|---|---|
| Reaction pressure | 1 atm |
| Reaction temperature | 280° C. |
| Reaction time | 1 h |
| Glycerin concentration | 28.1 wt %, 7.1 mol % |
| Feed flow | 3.5 ml/h |
| Diluent gas | nitrogen 40 ml/h |
| Catalyst amount | 0.1 g |

TABLE 2

Chemical formulae of catalysts prepared in examples and comparative examples, and glycerin conversion ratio and yield

| Example | Chemical Formula | Glycerin conversion ratio (%) | Acrolein yield (%) |
|---|---|---|---|
| Example 1 | $CuWS_3Ox$ | 18.0 | 4.4 |
| Example 2 | $CuB_{0.5}WS_3Ox$ | 5.6 | 0.8 |
| Example 3 | $CuBWS_3Ox$ | 8.5 | 1.4 |
| Example 4 | $NbBWP_2Ox$ | 16.1 | 3.5 |
| Example 5 | $NbBWP_2Ox$ | 13.6 | 2.9 |
| Example 6 | $Nb_{0.5}BWP_2Ox$ | 18.2 | 3.5 |
| Example 7 | $Nb_{0.7}BWP_2Ox$ | 11.9 | 2.6 |
| Example 8 | $NbB_{0.5}WP_2Ox$ | 10.4 | 2.0 |
| Example 9 | $NbB_{0.7}WP_2Ox$ | 9.8 | 3.5 |
| Example 10 | $Ce_{0.25}B_{0.25}WP_2Ox$ | 21.5 | 4.7 |
| Example 11 | $Ce_{0.25}B_{0.5}WP_2Ox$ | 22.3 | 6.1 |
| Example 12 | $Ce_{0.25}B_{0.75}WP_2Ox$ | 37.9 | 8.7 |
| Example 13 | $Ce_{0.25}BWP_2Ox$ | 44.6 | 13.4 |
| Example 14 | $Ce_{0.5}BWP_2Ox$ | 31.3 | 9.0 |
| Example 15 | $NbCeBWP_3Ox$ | 7.9 | 1.3 |
| Example 16 | $Cu_{0.2}B_{0.867}W_{0.5}POx$ | 10.5 | 2.9 |
| Comparative Example 1 | ZSM-5 [CBV28014] | 5.4 | 1.0 |
| Comparative Example 2 | Y-Zeolite [CBV901] | 13.8 | 0.8 |
| Comparative Example 3 | Mordenite [CBV21A] | 13.0 | 0.8 |
| Comparative Example 4 | $H_4SiW_{12}O_{40}$ | 3.9 | 0.2 |
| Comparative Example 5 | $H_3PW_{12}O_{40}$ | 4.2 | 0.2 |
| Comparative Example 6 | $BPO_4$ | 6.3 | 1.4 |

TABLE 3

Selectivity and Comparative selectivity of acrolein

| Example | Acrolein selectivity (%) | *Comparative selectivity 1 | **Comparative selectivity 2 |
|---|---|---|---|
| Example 1 | 24.3 | 0.6 | 2.0 |
| Example 2 | 13.4 | 0.8 | 4.7 |
| Example 3 | 16.6 | 1.3 | 4.3 |
| Example 4 | 21.6 | 1.0 | 2.6 |
| Example 5 | 21.5 | 1.4 | 3.0 |
| Example 6 | 19.5 | 1.4 | 3.3 |
| Example 7 | 21.5 | 1.1 | 2.7 |
| Example 8 | 19.3 | 1.1 | 3.4 |
| Example 9 | 25.4 | 0.7 | 2.0 |
| Example 10 | 21.8 | 1.1 | 2.5 |
| Example 11 | 27.4 | 1.2 | 2.2 |
| Example 12 | 23.0 | 1.1 | 2.4 |
| Example 13 | 30.0 | 1.0 | 1.8 |
| Example 14 | 28.8 | 0.7 | 1.6 |
| Example 15 | 16.8 | 1.2 | 3.1 |
| Example 16 | 27.1 | 0.8 | 2.0 |
| Comparative Example 1 | 18.8 | 1.3 | 3.9 |
| Comparative Example 2 | 5.7 | 2.1 | 13.3 |
| Comparative Example 3 | 6.4 | 3.3 | 12.5 |
| Comparative Example 4 | 6.1 | 3.4 | 10.8 |
| Comparative Example 5 | 4.0 | 4.0 | 17.3 |
| Comparative Example 6 | 21.5 | 2.1 | 3.3 |

*Comparative selectivity 1 = hydroxypropanone selectivity/acrolein selectivity
**Comparative selectivity 2 = (hydroxypropanone + propionaldehyde + propionic acid + aromatic compounds) selectivity/acrolein selectivity As shown in Tables 2 and 3, when the catalysts of the examples were used to react glycerin, high acrolein selectivity was observed, compared to use of the catalysts of the comparative examples, and comparative selectivity 1 or 2 which are ratios of by-product selectivity to selectivity of acrolein which is a main product as a target of the reaction was low, compared to use of the catalysts of the comparative examples.

These results indicate that the catalysts for glycerin dehydration of the examples can be used to prepare acrolein from glycerin with high selectivity and high purity and to inhibit formation of by-products such as hydroxypropanone, propionic acid, or aromatic compounds.

The invention claimed is:

1. A catalyst for glycerin dehydration, comprising a composite metal oxide represented by the following Chemical Formula 1:

$$(Ma)_p(Mb)_q WA_r O_x \quad \text{[Chemical Formula 1]}$$

wherein A is phosphorus or sulfur,
Ma and Mb are the same as or different from each other and are each independently Zr, Ti, Ce, Nb, Cr, Mn, Zn, B, or Cu, and p and q are a real number of 0 to 3, respectively,
when either one of Ma and Mb is B, the other is Zr, Ti, Ce, Nb, Cr, Mn, Zn, or Cu, and p and q are real numbers of more than 0 and 3 or less,
r is a real number of 1 to 3, and
x is a real number of 1 to 20.

2. The catalyst for glycerin dehydration of claim 1, wherein a molar ratio of phosphorus or sulfur and tungsten in the composite metal oxide is 10:1 to 1:10.

3. The catalyst for glycerin dehydration of claim 1, wherein a molar ratio of phosphorus or sulfur and tungsten, and oxygen in the composite metal oxide, is 1:1 to 1:5.

4. The catalyst for glycerin dehydration of claim 1, wherein a molar ratio of Ma or Mb and tungsten in the composite metal oxide is 10:1 to 1:10.

5. The catalyst for glycerin dehydration of claim 1, wherein if Ma and Mb in Chemical Formula 1 are the same as each other, Ma and Mb are Zr, Ti, Ce, Nb, Cr, Mn, Zn, or Cu.

6. The catalyst for glycerin dehydration of claim 1, wherein the composite metal oxide includes one or more selected from the group consisting of $CuWS_3O_x$, $CuBWS_3O_x$, $CuB_{0.4}WS_3O_x$, $NbBWP_2O_x$, $Nb_{0.5}BWP_2O_x$, $Nb_{0.7}BWP_2O_x$, $NbB_{0.5}WP_2O_x$, $NbB_{0.7}WP_2O_x$, $Ce_{0.25}B_{0.25}WO_2O_x$, $Ce_{0.25}B_{0.5}WP_2O_x$, $Ce_{0.25}B_{0.75}WP_2O_x$, $Ce_{0.25}BWP_2O_x$, $Ce_{0.5}BWP_2O_x$, $NbCeBWP_3O_x$, and $Cu_{0.2}B_{0.867}W_{0.5}PO_x$.

7. The catalyst for glycerin dehydration of claim 1, further comprising a support onto which the composite metal oxide is immobilized.

8. The catalyst for glycerin dehydration of claim 7, wherein the support is selected from the group consisting of silica, alumina, silica-alumina, zirconia, magnesia, magnesium aluminate, calcium aluminate, silicon carbide, zirconium phosphate, zeolite, and mixtures thereof.

9. The catalyst for glycerin dehydration of claim 7, wherein the support has a specific surface area (BET) of 10 to 500 $m^2/g$.

10. The catalyst for glycerin dehydration of claim 7, comprising 1 to 50 parts by weight of the composite metal oxide, based on 100 parts by weight of the support.

11. A preparation method of a catalyst for glycerin dehydration, comprising the steps of:
mixing one or more selected from the group consisting of a phosphorus precursor and a sulfur precursor, and one or more metal precursors selected from the group consisting of Zr, Ti, Ce, Nb, Cr, Mn, Zn, B, and Cu, with a tungsten precursor; and
drying and calcinating the mixture.

12. The preparation method of claim 11, wherein a mixing molar ratio of one or more selected from the group consisting of the phosphorus precursor and the sulfur precursor, and the tungsten precursor, is 10:1 to 1:10.

13. The preparation method of claim 11, wherein the calcinating step is performed at a temperature ranging from 100 to 900° C.

14. The preparation method of claim 11, wherein the calcinating step is performed for 10 minutes to 10 hours.

15. The preparation method of claim 11, further comprising the step of supporting the mixture on a support.

16. A preparation method of acrolein, comprising the step of reacting glycerin in the presence of the catalyst for glycerin dehydration of claim 1.

17. The preparation method of claim 16, wherein the dehydration is performed at a temperature of 200 to 400° C.

* * * * *